(12) United States Patent
Nagao et al.

(10) Patent No.: US 10,295,453 B2
(45) Date of Patent: May 21, 2019

(54) GAS-PHASE HYDROGEN PERMEATION TEST DEVICE AND METHOD OF PROTECTING GAS-PHASE HYDROGEN PERMEATION TEST DEVICE

(71) Applicant: JFE STEEL CORPORATION, Chiyoda-ku, Tokyo (JP)

(72) Inventors: Akihide Nagao, Tokyo (JP); Shusaku Takagi, Tokyo (JP)

(73) Assignee: JFE STEEL CORPORATION, Chiyoda-ku, Tokyo (JP)

( * ) Notice: Subject to any disclaimer, the term of this patent is extended or adjusted under 35 U.S.C. 154(b) by 66 days.

(21) Appl. No.: 15/556,940

(22) PCT Filed: Mar. 7, 2016

(86) PCT No.: PCT/JP2016/001228
§ 371 (c)(1),
(2) Date: Sep. 8, 2017

(87) PCT Pub. No.: WO2016/147595
PCT Pub. Date: Sep. 22, 2016

(65) Prior Publication Data
US 2018/0231450 A1    Aug. 16, 2018

(30) Foreign Application Priority Data

Mar. 19, 2015   (JP) .................................. 2015-056392

(51) Int. Cl.
*G01N 15/08*   (2006.01)

(52) U.S. Cl.
CPC ......... *G01N 15/0826* (2013.01); *G01N 15/08* (2013.01); *G01N 15/0806* (2013.01)

(58) Field of Classification Search
CPC . G01N 15/0826; G01N 15/0806; G01N 15/08
See application file for complete search history.

(56) References Cited

U.S. PATENT DOCUMENTS

| | | | |
|---|---|---|---|
| 3,590,634 A | 7/1971 | Pasternak et al. | |
| 8,117,899 B2 * | 2/2012 | Piombini | G01N 15/0826 73/38 |

(Continued)

FOREIGN PATENT DOCUMENTS

| | | |
|---|---|---|
| JP | S54104551 A | 8/1979 |
| JP | H0347706 B2 | 7/1991 |

(Continued)

OTHER PUBLICATIONS

May 10, 2016, International Search Report issued in the International Patent Application No. PCT/JP2016/001228.

(Continued)

*Primary Examiner* — Xin Y Zhong
(74) *Attorney, Agent, or Firm* — Kenja IP Law PC

(57) ABSTRACT

Provided is a gas-phase hydrogen permeation test device capable of safely measuring hydrogen permeation behavior in a material under a high-pressure hydrogen atmosphere. The gas-phase hydrogen permeation test device includes a high-pressure hydrogen feeder, an analyzer, a primary-side pipe, a secondary-side pipe, a secondary-side pressure gauge, a primary-side shut-off valve, a primary-side discharge valve, a secondary-side discharge valve, a passive discharger, a secondary-side shut-off valve, and a controller configured to, when the pressure measured by the secondary-side pressure gauge reaches or exceeds a specific value, place the primary-side shut-off valve and the secondary-side shut-off valve into a closed state and the primary-side discharge valve and the secondary-side discharge valve into an open state.

4 Claims, 1 Drawing Sheet

(56) References Cited

U.S. PATENT DOCUMENTS

2004/0123646 A1    7/2004   Echigo et al.
2005/0167598 A1*   8/2005   Bujas ................. G01N 15/0826
                                                                                    250/356.2

FOREIGN PATENT DOCUMENTS

| JP | 2005345342 A | 12/2005 |
| JP | 2012031021 A | 2/2012 |
| JP | 2013003028 A | 1/2013 |
| KR | 1020110044417 A | 4/2011 |
| WO | 2000028300 A1 | 5/2000 |

OTHER PUBLICATIONS

Takahiro Kushida , "Research on hydrogen embrittlement by electrochemical hydrogen permeation technique", Materials and Environment, 2000, pp. 195-200, vol. 49.
Apr. 13, 2018, Extended European Search Report issued by the European Patent Office in the corresponding European Patent Application No. 16764428.5.

* cited by examiner

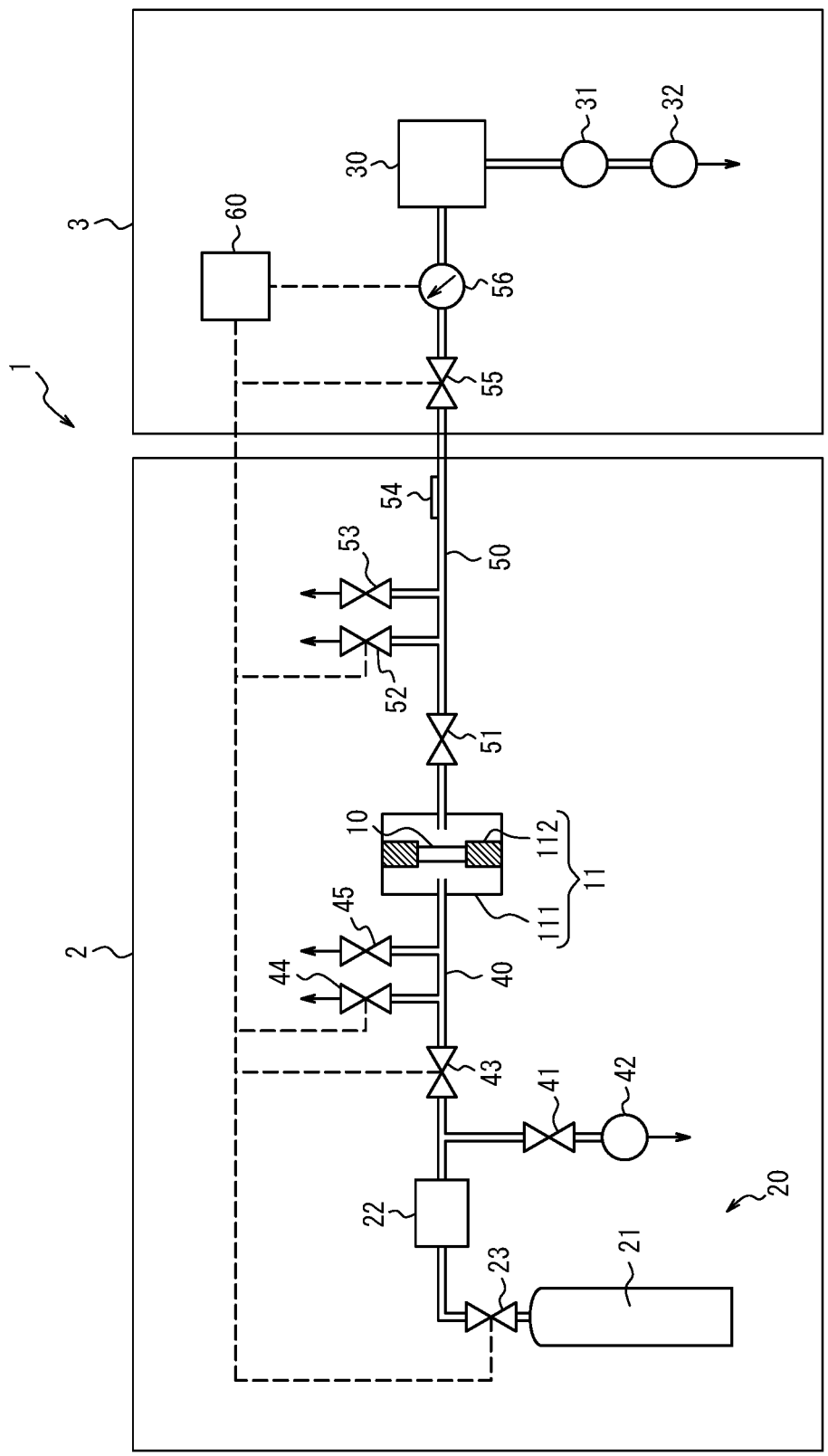

GAS-PHASE HYDROGEN PERMEATION TEST DEVICE AND METHOD OF PROTECTING GAS-PHASE HYDROGEN PERMEATION TEST DEVICE

TECHNICAL FIELD

This disclosure relates to a gas-phase hydrogen permeation test device, and more particularly to a gas-phase hydrogen permeation test device capable of safely measuring hydrogen permeation characteristics of a material under a high-pressure hydrogen gas atmosphere. This disclosure also relates to a method of protecting the gas-phase hydrogen permeation test device.

BACKGROUND

In recent years, hydrogen has attracted a great deal of attention worldwide as a clean energy source and from the perspective of diversification of energy. In particular, expectations are high for fuel cell vehicles using hydrogen gas as a fuel source, research related to the development of fuel cell vehicles has been widely progressed all over the world, and some fuel cell vehicles have already been put to practical use.

Fuel cell vehicles run with a hydrogen gas tank on-board, instead of on gasoline. Thus, development of hydrogen stations on behalf of gas stations is essential for the spread of fuel cell vehicles. In hydrogen stations, hydrogen is stored in a hydrogen pressure vessel, which is a container for high-pressure hydrogen, and hydrogen is charged from the pressure vessel to a hydrogen tank mounted on the fuel cell vehicle.

In order for a fuel cell vehicle to achieve a cruising distance comparable to that of a gasoline-powered vehicle, it is necessary to set the maximum filling pressure of the hydrogen tank mounted on the fuel cell vehicle to 70 MPa. It is thus required for an on-board hydrogen tank to be able to safely store and supply hydrogen under such a high-pressure hydrogen environment.

Similarly, in order to set the maximum filling pressure of the on-board hydrogen tank to 70 MPa, it is necessary to increase the maximum filling pressure of the hydrogen pressure vessel used at a hydrogen station to 82 MPa. From this follows that the hydrogen pressure vessel in the hydrogen station will be exposed to an ultra high-pressure hydrogen gas environment as high as 82 MPa.

Candidate materials to be used under such a high-pressure hydrogen environment include low alloy steel, stainless steel, aluminum alloy, plastic, and the like. However, when a steel material is used in a hydrogen environment, the strength decreases (hydrogen embrittlement) and, especially in low alloy steels, the drawability decreases.

Hydrogen embrittlement of a material occurs when hydrogen taken from the surrounding environment diffuses into the material and accumulates in a stress concentration part, a grain boundary, or the like. Therefore, the study of hydrogen permeation behavior in materials is very important, and research has thus flourished. For example, Takahiro Kushida, "*Materials and Environment*", Vol. 49 (2000), pp. 195-200 (NPL 1) describes an electrochemical hydrogen permeation method for investigating the behavior of hydrogen generated in solution permeating through a material. In addition, JPS54104551A (PTL 1) and JPH03047706B (PTL2) describe measurement of hydrogen permeation behavior in a material under a hydrogen gas environment.

CITATION LIST

Patent Literature

PTL 1: JPS54104551A
PTL 2: JPH03047706B

Non-Patent Literature

PTL 1: Takahiro Kushida, "*Materials and Environment*", Vol. 49 (2000), pp. 195-200

SUMMARY

Technical Problem

However, since the method described in NPL 1 is a test method conducted in solution, it is impossible to investigate the hydrogen permeation behavior under a hydrogen gas environment in which a pressure vessel and other components are actually used. In the methods described in PTLs 1 and 2, hydrogen permeation behavior in hydrogen gas can be measured.

However, the presently available data is given at a pressure of at most 150 atm, that is, 15.2 MPa, and tests under an ultra high-pressure hydrogen environment have not been conducted so far. The main reasons are as follows:

(1) Hydrogen itself, in its nature, can extremely easily cause an explosion; for example, it easily explodes in the state of being mixed with air in amounts of about 4% to 74%.

(2) For measurement of hydrogen permeation behavior in a material under an ultra high-pressure hydrogen environment, one face of a test piece (material) should be brought into contact with ultra high-pressure hydrogen gas, while the other should be placed in a reduced-pressure atmosphere in order to determine a trace amount of hydrogen with the analyzer. In particular, when the analyzer is a mass spectrometer, an ultra-high vacuum of about $10^{-7}$ Pa is required. As a result, it is necessary to maintain both an ultra-high-pressure hydrogen environment and an ultra-high vacuum environment through one thin test piece.

(3) Due to the pressure difference as described above, there is a risk of the test piece breaking during the test. When the test piece breaks, high-pressure hydrogen flows into the vacuum system, possibly destroying the analyzer and the accompanying vacuum pump and the like. Also, when hydrogen leaks to the outside and mixes with air, there is a danger of explosion by sparks or static electricity.

For the above reasons, it has not been possible to test the hydrogen permeation behavior in a material under an ultra-high-pressure environment as high as 82 MPa, for example, which is the pressure of the pressure vessel under consideration for practical application.

In view of the above circumstances, it would be helpful to provide a gas-phase hydrogen permeation test device capable of safely measuring hydrogen permeation behavior in a material under a high-pressure hydrogen atmosphere.

Solution to Problem

Main features of the present disclosure are described below.

1. A gas-phase hydrogen permeation test device for feeding high-pressure hydrogen to one face of a test piece and analyzing hydrogen permeating through the test piece and released from another face of the test piece, the gas-phase hydrogen permeation test device comprising: a high-pressure hydrogen feeder configured to feed high-pressure hydrogen to the one face of the test piece; an analyzer configured to analyze hydrogen released from the other face of the test piece; a primary-side pipe configured to connect the high-pressure hydrogen feeder to the one face of the test piece; a secondary-side pipe configured to connect the other face of the test piece to the analyzer; a secondary-side pressure gauge configured to measure pressure inside the secondary-side pipe; a primary-side shut-off valve provided in the primary-side pipe and configured to close the primary-side pipe when placed in a closed state; a primary-side discharge valve provided downstream of the primary-side shut-off valve in the primary-side pipe and configured to provide communication between the inside and outside of the primary-side pipe when placed in an open state; a secondary-side discharge valve provided in the secondary-side pipe and configured to provide communication between the inside and outside of the secondary-side pipe when placed in an open state; a passive discharger provided in the secondary-side pipe; a secondary-side shut-off valve provided downstream of the secondary-side discharge valve and the passive discharger in the secondary-side pipe and configured to close the secondary-side pipe when placed in a closed state; and a controller configured to, when the pressure measured by the secondary-side pressure gauge reaches or exceeds a specific value, place the primary-side shut-off valve and the secondary-side shut-off valve into a closed state and the primary-side discharge valve and the secondary-side discharge valve into an open state, wherein the primary-side shut-off valve, the primary-side discharge valve, and the secondary-side discharge valve are air-operated valves, the passive discharger is either or both of (i) a safety valve which is configured to be placed into an open state when the pressure inside the secondary-side pipe reaches or exceeds a specific value, and provide communication between the inside and outside of the secondary-side pipe, and (ii) a rupture disc which is configured to rupture when the pressure inside the secondary-side pipe reaches or exceeds a specific value, and provide communication between the inside and outside of the secondary-side pipe, the high-pressure hydrogen feeder, the primary-side pipe, the primary-side shut-off valve, the primary-side discharge valve, the passive discharger, the test piece, and the secondary-side discharge valve are installed in an explosion-proof environment, and the analyzer is installed in a non-explosion-proof environment.

2. The gas-phase hydrogen permeation test device according to 1., further comprising: an air-operated or manually-operated, secondary-side upstream shut-off valve provided upstream of the secondary-side discharge valve and the passive discharger in the secondary-side pipe and configured to close the secondary-side pipe when placed in a closed state.

3. A method of protecting the gas-phase hydrogen permeation test device as recited in 1. or 2., the method comprising: placing the primary-side shut-off valve and the secondary-side shut-off valve into a closed state and the primary-side discharge valve and the secondary-side discharge valve into an open state when the pressure measured by the secondary-side pressure gauge reaches or exceeds a specific value.

Advantageous Effect

According to the present disclosure, hydrogen gas does not break the device even when the test piece cannot withstand the pressure of the hydrogen gas and should be broken by any chance, which fact makes it possible to safely investigate the hydrogen permeation behavior in a material under a high-pressure hydrogen atmosphere.

BRIEF DESCRIPTION OF THE DRAWING

In the accompanying drawing,
FIG. 1 schematically illustrates an embodiment of the present disclosure.

DETAILED DESCRIPTION

An embodiment of the present disclosure will be described below. Unless otherwise noted, all pressure values given below are gauge pressures. The gas-phase hydrogen permeation test device according to an embodiment of the present disclosure comprises: a high-pressure hydrogen feeder configured to feed high-pressure hydrogen to one face of a test piece; an analyzer configured to analyze hydrogen released from the other face of the test piece; a primary-side pipe configured to connect the high-pressure hydrogen feeder to the one face of the test piece; a secondary-side pipe configured to connect the other face of the test piece to the analyzer; a secondary-side pressure gauge configured to measure pressure inside the secondary-side pipe; a primary-side shut-off valve provided in the primary-side pipe and configured to close the primary-side pipe when placed in a closed state; a primary-side discharge valve provided downstream of the primary-side cutoff valve in the primary-side pipe and configured to provide communication between the inside and outside of the primary-side pipe when placed in an open state; a secondary-side discharge valve provided in the secondary-side pipe and configured to provide communication between the inside and outside of the secondary-side pipe when placed in an open state; a passive discharger provided in the secondary-side pipe; a secondary-side shut-off valve provided downstream of the secondary-side discharge valve and the passive discharger in the secondary-side pipe and configured to close the secondary-side pipe when placed in a closed state; and a controller configured to, when the pressure measured by the secondary-side pressure gauge reaches or exceeds a specific value, place the primary-side shut-off valve and the secondary-side shut-off valve into a closed state and the primary-side discharge valve and the secondary-side discharge valve into an open state, wherein the primary-side shut-off valve, the primary-side discharge valve, and the secondary-side discharge valve are air-operated valves, the passive discharger is either or both of (i) a safety valve which is configured to be placed into an open state when the pressure inside the secondary-side pipe reaches or exceeds a specific value, and provide communication between the inside and outside of the secondary-side pipe, and (ii) a rupture disc which is configured to rupture when the pressure inside the secondary-side pipe reaches or exceeds a specific value, and provide communication between the inside and outside of the secondary-side pipe, the high-pressure hydrogen feeder, the primary-side pipe, the primary-side shut-off valve, the primary-side discharge valve, the passive discharger, the test piece, and the secondary-side discharge valve are installed in an explosion-proof environment, and the analyzer is installed in a non-explosion-proof environment.

The above-identified components of the gas-phase hydrogen permeation test device may be configured as described below.

[Test Piece]

As a test piece for testing the permeation behavior of hydrogen, a test piece made of any material such as metal may be used. Examples of the material include steel such as low-alloy steel. The shape of the test piece is not particularly limited, and it may be of any shape such as a disk-like shape. When a test piece in the form of a disk is used, its diameter is preferably, for example, 10 mm to 100 mm, and more preferably 20 mm to 80 mm. The thickness of the test piece is also not particularly limited, yet it is preferably 0.1 mm to 10 mm, and more preferably 2 mm to 8 mm, from the perspectives of, for example, pressure resistance and time required for hydrogen permeation. In the test, after mechanically polishing the surface of a test piece 10, it is preferable to perform chemical polishing or electropolishing to remove the processed layer formed by the mechanical polishing from the surface of the test piece. Further, for example, the surface of the test piece may be coated with a metal, such as Pd or Ni, using a method such as plating or vapor deposition, on the side from which hydrogen enters (primary-side) or the side from which hydrogen is released (secondary-side).

The test piece is held with both surfaces sealed so that one surface exposed to high-pressure hydrogen and the other exposed to a reduced pressure environment are kept airtight, respectively. As the seal, a metal O-ring, a metal gasket, or the like is preferably used.

Further, since the test piece is exposed to high-pressure hydrogen and a reduced-pressure environment, the test piece is preferably held in a test piece holder having a strength and extremely high airtightness capable of withstanding these environments. In particular, the test piece holder has strength such that it can withstand a high-pressure condition on the side where the surface of the test piece exposed to high-pressure hydrogen is held, and a reduced-pressure condition on the side where the test piece exposed to a reduced-pressure (possibly ultra-high-vacuum) environment is held. The test piece holder also has airtightness such that it can prevent high-pressure hydrogen inside the test piece holder from leaking to the outside and the external air from entering into the test piece holder during the test. As this test piece holder, arbitrary ones including those well known in the art may be used. In particular, from the perspectives of low gas release at elevated temperature, high airtightness, high strength, good workability, cost, and so on, the test piece holder is preferably made of stainless steel used in ultra high-vacuum application, such as austenitic stainless steel.

Further, the test piece holder may be provided with a test piece holding jig configured to actually hold the test piece and an airtight chamber configured to contain the test piece holding jig. On the other hand, by providing the test piece holding jig itself with necessary strength and airtightness, it is also possible to provide the test piece holder with the test piece holding jig alone, without the airtight chamber. In addition to the airtight chamber and the test piece holding jig, the test piece holder may be provided with a temperature adjuster configured to keep the temperature of the test piece constant during the test. The temperature adjuster comprises, for example, a heater configured to set the temperature of the test piece above room temperature, a cooler configured to set the temperature of the test piece below room temperature, a temperature measuring device configured to measure the temperature of the test piece, and a temperature controller configured to feed back the measurement results obtained by the temperature measuring device to the heater or cooler and to control the temperature of the test piece to the set temperature. As the temperature adjuster, arbitrary methods and devices may be appropriately selected and used. The temperature adjuster may also be used to keep the ambient temperature of the test piece as well as the temperature of the test piece constant.

[High-Pressure Hydrogen Feeder]

A high-pressure hydrogen feeder is installed on a side that is connected to one face of the test piece from which hydrogen enters (this side will be referred to as "primary side"). The high-pressure hydrogen feeder may be of any type as long as it can supply hydrogen at a pressure required for the test. One example may be a device that enables hydrogen gas taken out from a hydrogen cylinder to be supplied at a desired pressure through compression by a compressor.

[Analyzer]

An analyzer is installed on a side that is connected to another face of the test piece from which hydrogen is released (this side will be referred to as "secondary side") in order to detect and quantify a trace amount of hydrogen gas permeating through the test piece. As the analyzer, for example, a mass spectrometer or a gas chromatograph may be used.

When a mass spectrometer is used as the analyzer, for example, a quadrupole mass spectrometer (QMS), a magnetic deflection mass spectrometer, or a time-of-flight mass spectrometer (TOF-MS) may be used. Specifically, it is preferable to use a device capable of continuously measuring hydrogen at constant time intervals, for example, at intervals of 10 seconds.

Preferably, the gas-phase hydrogen permeation test device further comprises a pump (vacuum pump) for depressurizing the space between the secondary-side surface of the test piece and the mass spectrometer, such as inside the secondary-side pipe as described later. By using the vacuum pump, the amount of background hydrogen which would otherwise interfere with quantification can be reduced, and the accuracy of measurement can be improved. When the pressure reduction is performed by the pump, it is preferable to set the secondary side to a high vacuum of $1.0 \times 10^{-5}$ Pa or less. The pump may be of any type, yet for example a combination of a rotary pump and a turbo molecular pump may be used. In addition to this combination, to increase the degree of vacuum, a non-evaporable getter pump, a sputter ion pump, or the like may be used. Such pumps may be used either in singular or plural form. The degree of vacuum on the secondary side is preferably as low as possible. Specifically, it is more preferably $1.0 \times 10^{-6}$ Pa or less, and still more preferably $1.0 \times 10^{-7}$ Pa or less. The lower limit for the secondary-side pressure is not particularly limited, yet, practically, it is not necessary to reduce the secondary-side pressure below $1.0 \times 10^{-12}$ Pa.

When a gas chromatograph is used as the analyzer, a detector capable of detecting hydrogen is used, such as a thermal conductivity detector, a hydrogen flame ionization detector, a helium plasma ionization detector, an electron capture detector, a photoionization detector, or a flame photometric detector. The quantification of hydrogen using a gas chromatograph may be performed at a desired point in time, for example, it may be performed at a point in time when the amount of hydrogen permeation reaches a certain steady state, or continuously at constant time intervals such as every five minutes.

When a chromatograph is used, a carrier gas that carries hydrogen released from the material to the detector is used. The carrier gas may be selected from among gases suitable for the detector used, and, for example, may be argon gas for a thermal conductivity detector or helium gas for a hydrogen flame ionization detector. The purity of the carrier gas is desirably as high as possible, and is preferably 5 N (99.999 vol %) or more, and more preferably 6 N (99.9999 vol %) or more.

[Pipe]

In the gas-phase hydrogen permeation test device, the high-pressure hydrogen feeder and one face of the test piece are connected to each other through a primary-side pipe. Further, the other side of the test piece and the analyzer are connected to each other through a secondary-side pipe. For the primary- and secondary-side pipes, pipes made of a material such as metal in accordance with the corresponding working pressure may be appropriately selected and used. For the secondary-side pipe, it is desirable to reduce internal volume as much as possible to achieve high vacuum. For the sake of cleanliness, it is also preferable to use, for example, a tube made of stainless steel and electropolished on its inner surface.

As used herein, the phrase "the high-pressure hydrogen feeder and one face of the test piece are connected through the primary-side pipe" indicates a state in which high-pressure hydrogen fed from the high-pressure hydrogen feeder is adapted to be able to reach one side of the test piece. In other words, this phrase refers to not only a state in which one end of the primary-side pipe and one face of the test piece are in direct contact, but also a state in which, for example, the one end of the primary-side pipe is connected to a side on which the one face of the test piece is located in the test piece holder so that the high-pressure hydrogen is fed to the one face within the test piece holder.

Similarly, the phrase "another face of the test piece and the analyzer are connected to each other through the secondary-side pipe" indicates a state in which hydrogen released from the other face of the test piece is adapted to be able to reach the analyzer. In other words, this phrase refers to not only a state in which the other face of the test piece and one end of the secondary-side pipe are in direct contact, but also a state in which, for example, the one end of the secondary-side pipe is connected to a side on which the other face of the test piece is located in the test piece holder so that the hydrogen released from the other face is transferred from the test piece holder to the analyzer.

[Secondary-Side Pressure Gauge]

The secondary-side pipe is provided with a secondary-side pressure gauge configured to measure pressure inside the secondary-side pipe. In the gas-phase hydrogen permeation test device disclosed herein, pressure is measured using the secondary-side pressure gauge, and when the pressure is equal to or higher than a specific reference, it is judged that the test piece has broken, and valve opening and closing operation is performed to ensure safety, as will be described later. The secondary-side pressure gauge is not limited to a particular type, and may be of any type as long as it can detect a pressure rise upon breakage of the test piece. Measurement of pressure with the secondary-side pressure gauge may be performed intermittently such as at constant time intervals, yet is preferably performed continuously at all times.

[Shut-Off Valve]

The primary- and secondary-side pipes are respectively provided with shut-off valves (primary-side shut-off valve and secondary-side shut-off valve). In performing a test using the gas-phase hydrogen permeation test device, the primary-side shut-off valve may be in an open state when the primary side is pressurized and be placed into a closed state after completion of the pressurization. In addition, the secondary-side shut-off valve may be always opened when the test proceeds normally.

However, when the test piece breaks and high-pressure hydrogen on the primary-side flows into the secondary-side, an abnormality is detected as a rise in the pressure inside the secondary-side pressure gauge, and if the pressure measured by the secondary-side pressure gauge is equal to or higher than a predetermined reference, the primary- and secondary-side shut-off valves are placed into a closed state by the controller. When the primary-side shut-off valve is closed, the hydrogen gas fed from the high-pressure hydrogen feeder does not advance to the downstream side of the primary-side shut-off valve, making it possible to prevent further high-pressure hydrogen from flowing into the secondary side. In addition, the closure of the secondary-side shut-off valve can prevent the hydrogen gas flowing into the secondary-side pipe from entering and damaging the analyzer or the vacuum pump connected to the analyzer.

[Discharge Valve]

Similarly, the primary- and secondary-side pipes are respectively provided with discharge valves (primary-side discharge valve and secondary-side discharge valve). The discharge valves are normally in a closed state, yet when the pressure measured by the secondary-side pressure gauge is equal to or higher than a specific reference, they are placed into an open state by the controller. When the primary- and secondary-side discharge valves are opened, high-pressure hydrogen gases inside the primary- and secondary-side pipes are promptly discharged to the outside, making it possible to prevent high-pressure gas from entering and damaging the downstream analyzer. In addition, the primary-side shut-off valve, which is provided upstream of the primary- and secondary-side discharge valves, is closed when the primary- and secondary-side discharge valves are opened. Thus, the high-pressure hydrogen gas cannot be discharged to the outside of the device in amounts greater than that present in the pipe at the time the primary-side shut-off valve is closed.

In addition to the above shut-off valves and discharge valves, valves of an arbitrary structure may be provided at arbitrary positions without impairing the functions of the present disclosure.

[Controller]

The shut-off valves and the discharge valves are opened and closed by a controller. When the pressure measured by the secondary-side pressure gauge reaches or exceeds a specific value, the controller controls opening and closing operations so that the primary- and secondary-side shut-off valves are placed into a closed state and the primary- and secondary-side discharge valves into an open state.

[Passive Discharger]

The gas-phase hydrogen permeation test device further comprises a passive discharger provided upstream of the secondary-side shut-off valve in the secondary-side pipe. As used herein, the passive discharger refers to such a discharger that has a function of releasing the gas in the pipe when a specific condition is satisfied in an automatic manner, namely, independently of the secondary-side pressure gauge or the controller separately provided. Specifically, either or both of the safety valve and the rupture disk are used as the passive discharger. The safety valve, which is also called a relief valve, is placed into an open state to discharge the gas in the pipe to the outside only when the pressure inside the pipe reaches or exceeds a specific value by the action of a spring or the like. In addition, the rupture disk, which is also called a bursting disk and is a member made of a thin metal plate or the like, has a function of breaking and discharging the gas in the pipe to the outside when the pressure inside the pipe reaches or exceeds a set value. The safety valve and the rupture disk are not limited to a particular type, and may be appropriately selected and used in accordance with the conditions under which the device is used, such as pressure.

According to the present disclosure, using the discharge valve controlled by the secondary-side pressure gauge and the controller in combination with the passive discharger ensures that any high-pressure hydrogen gas flowing into the secondary side upon breakage of the test piece can be surely and promptly discharged to the outside, preventing breakage of the analyzer or the like. The safety valve and the rupture disk used as the passive discharger are both passive type dischargers that do not require control by an external controller nor power supply, and hence they are able to ensure safety without losing their functionality should the discharge valve fail to operate for some reason, such as power failure or breakdown. In addition, it is preferable to install both the safety valve and the rupture disk because this setup contributes to further improvement of redundancy.

[Explosion-Proof Environment/Non-Explosion-Proof Environment]

In the gas-phase hydrogen permeation test device, as described above, when the test piece breaks, the release valve is opened to discharge hydrogen gas to the surroundings. Therefore, for example, if a spark occurs around the gas-phase hydrogen permeation test device, hydrogen gas mixed with the surrounding air may explode. To prevent this, in the present disclosure, portions where high-pressure hydrogen is handled, as well as portions from which high-pressure hydrogen is possibly released, specifically, the high-pressure hydrogen feeder, the primary-side pipe, the primary-side shut-off valve, the primary-side discharge valve, the passive discharger, the test piece, and the secondary-side discharge valve are installed in an explosion-proof environment. As the explosion-proof environment, for example, an explosion-proof chamber may be used. In addition, each item installed in the explosion-proof environment shall be designed to explosion-proof specifications. On the other hand, the analyzer is installed in a non-explosion-proof environment. Therefore, the upstream part (test piece side) of the secondary pipe is arranged in the explosion-proof environment, while the downstream part (analyzer side) in the non-explosion-proof environment. The secondary-side pressure gauge and the secondary-side shut-off valve may be installed in the explosion-proof environment or the non-explosion-proof environment. However, for installation in the explosion-proof environment, it is necessary to design them to explosion-proof specifications. Thus, the secondary-side pressure gauge and the secondary-side shut-off valve are preferably installed in the non-explosion-proof environment. As an explosion-proof shut-off valve, an air-operated valve described later may be used.

It is noted here that the members and devices other than those described above as being included in the gas-phase hydrogen permeation test device, as well as other devices installed in combination with the gas-phase hydrogen permeation test device may basically be installed in the explosion-proof or non-explosion-proof environment, provided that those not designed to explosion-proof specifications shall be installed in the non-explosion-proof environment and those in need for installation in the explosion-proof environment shall be designed to explosion-proof specifications.

[Valve Drive Mechanism]

Among the valves of the gas-phase hydrogen permeation test device, at least the primary-side shut-off valve, the primary-side discharge valve, and the secondary-side discharge valve are air-driven valves (air-operated valve). These valves are installed in the explosion-proof environment, into which high-pressure hydrogen is released upon breakage of the test piece. Thus, by using air-operated valves as these valves, explosion can be prevented upon release of hydrogen. In this way, a mechanism for discharging hydrogen, such as a discharge valve, is combined with an air-operated valve in the explosion-proof environment according to the present disclosure, allowing high-pressure hydrogen gas to be safely discharged to the outside even upon breakage of the test piece and preventing damage to the analyzer or the like. An arbitrary drive mechanism may be used for valves other than the primary-side shut-off valve, the primary-side release valve, and the secondary-side release valve, provided that those installed in the explosion-proof environment shall be designed to explosion-proof specifications, such as air-operated, manually-operated, or explosion-proof and electromagnetic (solenoid-operated) type.

In the gas-phase hydrogen permeation test device, it is preferable to further provide a secondary-side upstream shut-off valve on the upstream side of the secondary-side discharge valve and the passive discharger in the secondary-side pipe. The secondary-side upstream shut-off valve is configured to close the secondary-side pipe in a closed state, and is of air-operated or manually-operated type. In the test device disclosed herein, it is necessary to keep the inside of the vacuum system on the secondary side clean in order to maintain the detection accuracy of a trace amount of hydrogen. When no test piece is attached, however, the test piece side of the secondary-side pipe is placed in an open state, and outside air may enter the secondary-side pipe. In view of this, as described above, the secondary-side upstream shut-off valve is provided, and the secondary-side upstream shut-off valve is closed when no test piece is attached, such as when the test piece is replaced or when the device is not in use. This setup makes it possible to prevent outside air from flowing into the downstream side of the secondary-side upstream shut-off valve.

Embodiments of the present disclosure will be specifically described with reference to the accompanying drawings. The following provides a description of some of the preferred embodiments of the present disclosure, by way of example only, and the present disclosure is by no means limited to the disclosed embodiments.

FIG. 1 schematically illustrates one of the embodiments of the present disclosure. A gas-phase hydrogen permeation test device 1 is installed across an explosion-proof chamber 2 and a non-explosion-proof chamber 3, and comprises a test piece 10, a high-pressure hydrogen feeder 20, and a quadrupole mass spectrometer 30. The test piece 10 is a disk-shaped metal which may be, for example, a steel sheet.

The test piece 10 is held by the test piece holder 11. The test piece holder 11 comprises an airtight chamber 111 and a test piece holding jig 112. The test piece 10 is held and fixed in the airtight chamber 111 by the test piece holding jig 112, and sealed on both sides by a metal O ring (not shown).

The high-pressure hydrogen feeder 20 comprises a hydrogen cylinder 21 and a compressor 22. To the cylinder 21 is attached an air-operated valve shutter 23. The high-pressure hydrogen feeder 20 is connected through a primary-side pipe 40 to a side of one face of the test piece 10 in the test piece holder 11. This primary-side pipe 40 allows high-pressure hydrogen to be sent from the high-pressure hydrogen feeder 20 to the one face of the test piece 10. Furthermore, as illustrated in FIG. 1, to the primary-side pipe 40 are attached, in upstream to downstream order, an air-operated valve 41, a rotary pump 42, an air-operated valve 43, an air-operated valve 44, and a safety valve 45. The rotary pump 42 is used to exhaust gases from the primary-side pipe at the beginning of use of the device. Further, the air-operated valves 43 and 44 function as the primary-side shut-off valve and the primary-side discharge valve, respectively. In this embodiment, assuming that the test is performed with the pressure on the primary side raised to 110 MPa, pressure resistance was set to 110 MPa for each valve connected to the primary-side pipe 40.

To the quadrupole mass spectrometer 30 as the analyzer are connected a turbo molecular pump 31 and a rotary pump 32 that are used to reduce the pressure inside the quadrupole mass spectrometer and in the secondary-side pipe. The quadrupole mass spectrometer 30 is connected through a secondary-side pipe 50 to a side of the other face of the test piece 10 in the test piece holder 11. This secondary-side pipe 50 allows hydrogen released from the other face of the test piece 10 to be transferred to the quadrupole mass spectrometer 30. Furthermore, as illustrated in FIG. 1, to the secondary pipe 50 are attached, in upstream to downstream order, an air-operated valve 51, an air-operated valve 52, a safety valve 53, a rupture disk 54, an air-operated valve 55, and a secondary-side pressure gauge 56. The air-operated valves 51, 52, and 55 function as a secondary-side upstream shut-off valve, a secondary-side discharge valve, and a secondary-side shut-off valve, respectively. In this embodiment, for the valves and rupture disks connected to the secondary-side pipe 50, the following pressure resistance was selected: 0.1 MPa for the air-operated valve 51; 8 MPa for the air-operated valve 52; 0.2 MPa for the safety valve 53; 0.45 MPa for the rupture disk 54; and 0.1 MPa for the air-operated valve 55. As valves generally increase in size with pressure resistance, it is preferable to avoid using a valve having a higher pressure resistance than necessary in order to achieve a high vacuum on the secondary side.

To the secondary-side pressure gauge 56 is connected a controller 60, which in turn is connected to a valve shutter 23, an air-operated valve 43 (primary-side shut-off valve), an air-operated valve 44 (primary-side discharge valve), an air-operated valve 52 (secondary-side discharge valve), and an air-operated valve 55 (secondary-side shut-off valve). Opening and closing operations of the valve shutter and the air-operated valves are performed by controlling the supply of air from a compressed air feeder (not shown) using an electromagnetic valve provided in the controller 60.

The dimension of the test piece holder 11 is not particularly limited as long as it can accommodate the test piece and can provide connection between the primary-side pipe 40 and the secondary-side pipe 50. However, if the internal volume of the test piece holder 11 is excessively large, the quantitative accuracy of hydrogen provided by the quadrupole mass spectrometer 30 may decrease. Thus, the dimension of the test piece holder 11 is preferably determined in consideration of the resolution and analysis limit of the quadrupole mass spectrometer 30.

The following provides a description of the operation of the gas-phase hydrogen permeation test device 1 according to this embodiment. In the following description, it is assumed that the discharge valves (air-operated valves 44 and 52) and safety valves 45 and 53, which are provided for safety measures in case of breakage of the test piece, are always in a closed state except when the test piece breaks.

In using the gas-phase hydrogen permeation test device 1 according to this embodiment, the test piece 10 is first set in the test piece holder 11 while the air-operated valve 51 as the secondary-side upstream shut-off valve is closed, and then gases are exhausted from the primary-side pipe 40 and the secondary-side pipe 50. Exhaust of gases from the primary-side pipe 40 is carried out by the rotary pump 42, with the valve shutter 23 placed in a closed state and the air-operated valve 41 in an open state. Exhaust of gases from the secondary-side pipe 50 is carried out by the turbo molecular pump 31 and the rotary pump 32, with the air-operated valve 51 placed in an open state.

After a desired degree of vacuum is reached, the rotary pump 42 is stopped and the air-operated valve 41 is closed to terminate the exhaust of gases from the primary side. Then, the valve shutter 23 is opened, and the compressor 22 is operated to feed high-pressure hydrogen into the primary-side pipe 40. After the pressure inside the primary-side pipe reaches a desired pressure, the valve shutter 23 and the air-operated valve 43 are closed, and the supply of hydrogen is stopped. On the other hand, on the secondary side, measurement is made with the quadrupole mass spectrometer 30 of hydrogen that has permeated through the test piece 10 and discharged into the secondary-side pipe 50. The measurement may be performed continuously, for example, every 10 seconds. In this way, hydrogen permeation characteristics of the test piece 10 can be evaluated.

In the gas-phase hydrogen permeation test device 1 according to this embodiment, the pressure inside the secondary-side pipe 50 is continuously monitored using the secondary-side pressure gauge 56. Should the test piece break during the test, high-pressure hydrogen on the primary side flows into the secondary side and the pressure inside the secondary-side pipe 50 rises. As such, breakage of the test piece 10 can be detected by the secondary-side pressure gauge 56. When the pressure measured by the secondary-side pressure gauge 56 reaches or exceeds a predetermined threshold, it is considered that the test piece has broken, and the air-operated valves 43 and 55 as the shut-off valves are placed into a closed state and the air-operated valves 44 and 52 as the discharge valves into an open state. Additionally, the valve shutter 23 attached to the hydrogen cylinder 21 is placed into a closed state to terminate the supply of hydrogen from the cylinder. At this point, if the air-operated valve or the valve shutter as the shut-off valve is already in a closed state, it may be left as it is. The above operations are performed simultaneously by the controller 60 connected to the secondary pressure gauge 50.

Furthermore, when the pressure inside the secondary-side pipe 50 reaches and exceeds a specific pressure, the safety valve 53 is placed into an open state and the rupture disk 54 ruptures to provide communication between the secondary-side pipe 50 and the outside, allowing high-pressure hydrogen flowing into the secondary side to be discharged to the outside. The safety valve 53 and the rupture disk 54 operate in an automatic manner, independently of the controller.

Apart from the above operation, when the pressure inside the primary-side pipe rises for some reason and reaches or exceeds a predetermined value, the safety valve 45 is placed into an open state to provide communication between the inside of the primary-side pipe 40 and the outside, allowing high-pressure hydrogen to be discharged to the outside.

In this way, providing the passive discharger in addition to the shut-off valves and discharge valves, which are controlled on the basis of the pressure on the secondary side, may reliably prevent high-pressure hydrogen from flowing into the secondary side and damaging the analyzer or the like upon breakage of the test piece. Since the primary-side pipe, the primary-side shut-off valve, the primary-side discharge valve, the passive discharger, the test piece, and the secondary-side discharge valve are installed in the explosion-proof chamber 2, it is possible to prevent the occurrence of explosion resulting from leakage of hydrogen from, for example, the primary-side pipe 40 or the test piece holder 11, or explosion resulting from discharge of hydrogen from the discharge valve, the safety valve, or the rupture disk upon breakage of the test piece. Therefore, the gas-phase hydrogen permeation test device according to the disclosure enables measurement of hydrogen permeation behavior in materials in a remarkably safe manner under a high-pressure hydrogen atmosphere, which conventionally was difficult.

REFERENCE SIGNS LIST

1 Gas-phase hydrogen permeation test device
2 Explosion-proof chamber
3 Non-explosion-proof chamber
10 Test piece
11 Test piece holder
111 Airtight chamber
112 Test piece holding jig
20 High-pressure hydrogen feeder
21 Hydrogen cylinder
22 Compressor
23 Valve shutter
30 Quadrupole mass spectrometer (analyzer)
31 Turbo molecular pump
32 Rotary pump
40 Primary-side pipe
41 Air-operated valve
42 Rotary pump
43 Air-operated valve (primary-side shut-off valve)
44 Air-operated valve (primary-side discharge valve)
45 Safety valve
50 Secondary-side pipe
51 Air-drive valve (secondary-side upstream shut-off valve)
52 Air-operated valve (secondary-side discharge valve)
53 Safety valve (passive discharger)
54 Rupture disk (passive discharger)
55 Air-operated valve (secondary-side shut-off valve)
56 Secondary-side pressure gauge
60 Controller

The invention claimed is:

1. A gas-phase hydrogen permeation test device for feeding high-pressure hydrogen to one face of a test piece and analyzing hydrogen permeating through the test piece and released from another face of the test piece, the gas-phase hydrogen permeation test device comprising:
a high-pressure hydrogen feeder configured to feed high-pressure hydrogen to the one face of the test piece;
an analyzer configured to analyze hydrogen released from the other face of the test piece;
a primary-side pipe configured to connect the high-pressure hydrogen feeder to the one face of the test piece;
a secondary-side pipe configured to connect the other face of the test piece to the analyzer;
a secondary-side pressure gauge configured to measure pressure inside the secondary-side pipe;
a primary-side shut-off valve provided in the primary-side pipe and configured to close the primary-side pipe when placed in a closed state;
a primary-side discharge valve provided downstream of the primary-side shut-off valve in the primary-side pipe and configured to provide communication between the inside and outside of the primary-side pipe when placed in an open state;
a secondary-side discharge valve provided in the secondary-side pipe and configured to provide communication between the inside and outside of the secondary-side pipe when placed in an open state;
a passive discharger provided in the secondary-side pipe;
a secondary-side shut-off valve provided downstream of the secondary-side discharge valve and the passive discharger in the secondary-side pipe and configured to close the secondary-side pipe when placed in a closed state; and
a controller configured to, when the pressure measured by the secondary-side pressure gauge reaches or exceeds a specific value, place the primary-side shut-off valve and the secondary-side shut-off valve into a closed state and the primary-side discharge valve and the secondary-side discharge valve into an open state,
wherein
the primary-side shut-off valve, the primary-side discharge valve, and the secondary-side discharge valve are air-operated valves,
the passive discharger is either or both of (i) a safety valve which is configured to be placed into an open state when the pressure inside the secondary-side pipe reaches or exceeds a specific value, and provide communication between the inside and outside of the secondary-side pipe, and (ii) a rupture disc which is configured to rupture when the pressure inside the secondary-side pipe reaches or exceeds a specific value, and provide communication between the inside and outside of the secondary-side pipe,
the high-pressure hydrogen feeder, the primary-side pipe, the primary-side shut-off valve, the primary-side discharge valve, the passive discharger, the test piece, and the secondary-side discharge valve are installed in an explosion-proof environment, and
the analyzer is installed in a non-explosion-proof environment.

2. The gas-phase hydrogen permeation test device according to claim 1, further comprising: an air-operated or manually-operated, secondary-side upstream shut-off valve provided upstream of the secondary-side discharge valve and the passive discharger in the secondary-side pipe and configured to close the secondary-side pipe when placed in a closed state.

3. A method of protecting the gas-phase hydrogen permeation test device as recited in claim 1, the method comprising: placing the primary-side shut-off valve and the secondary-side shut-off valve into a closed state and the primary-side discharge valve and the secondary-side discharge valve into an open state when the pressure measured by the secondary-side pressure gauge reaches or exceeds a specific value.

4. A method of protecting the gas-phase hydrogen permeation test device as recited in claim 2, the method comprising: placing the primary-side shut-off valve and the secondary-side shut-off valve into a closed state and the primary-side discharge valve and the secondary-side discharge valve into an open state when the pressure measured by the secondary-side pressure gauge reaches or exceeds a specific value.

* * * * *